United States Patent [19]

Natelson

[11] 4,004,150
[45] Jan. 18, 1977

[54] ANALYTICAL MULTIPLE COMPONENT READOUT SYSTEM

[76] Inventor: Samuel Natelson, 5438 N. Artesian Ave., Chicago, Ill. 60625

[22] Filed: May 1, 1975

[21] Appl. No.: 573,766

[52] U.S. Cl. .............................. 250/328; 250/365; 250/373; 250/428; 250/432 R; 250/576

[51] Int. Cl.² .................... G01T 1/00; G01N 21/26

[58] Field of Search .......... 250/373, 372, 564, 565, 250/328, 576, 428, 432, 578, 365

[56] References Cited

UNITED STATES PATENTS

| 1,746,525 | 2/1930 | Darrah | 250/564 |
| 2,043,589 | 6/1936 | Muller | 250/564 |
| 2,066,934 | 1/1937 | Gulliksen | 250/564 |
| 3,322,956 | 5/1967 | Shah | 250/564 |
| 3,381,135 | 4/1968 | Keller | 250/565 |
| 3,489,525 | 1/1970 | Natelson | 23/253 R |
| 3,773,426 | 11/1973 | Mudd | 250/564 |
| 3,854,050 | 12/1974 | Peterson et al. | 250/328 |

Primary Examiner—Harold A. Dixon
Attorney, Agent, or Firm—George B. Oujevolk

[57] ABSTRACT

The present invention contemplates an arrangement for analyzing a plurality of components in a single specimen which comprises placing a diluted specimen into a storage cup which is part of a sample carrier system, containing storage and reaction cups, transferring aliquots of the diluted solutions of the sample from the storage to the reaction cups, presenting the rows of the reaction cups to a work station, sequentially, adding a reagent to each of the reaction cups and moving the reaction cups into a work field where beams of light passing through the various reaction cups can be scanned and the components contained in the reaction cups can be assayed by means of a single detector attached to a computer and print-out system.

15 Claims, 14 Drawing Figures

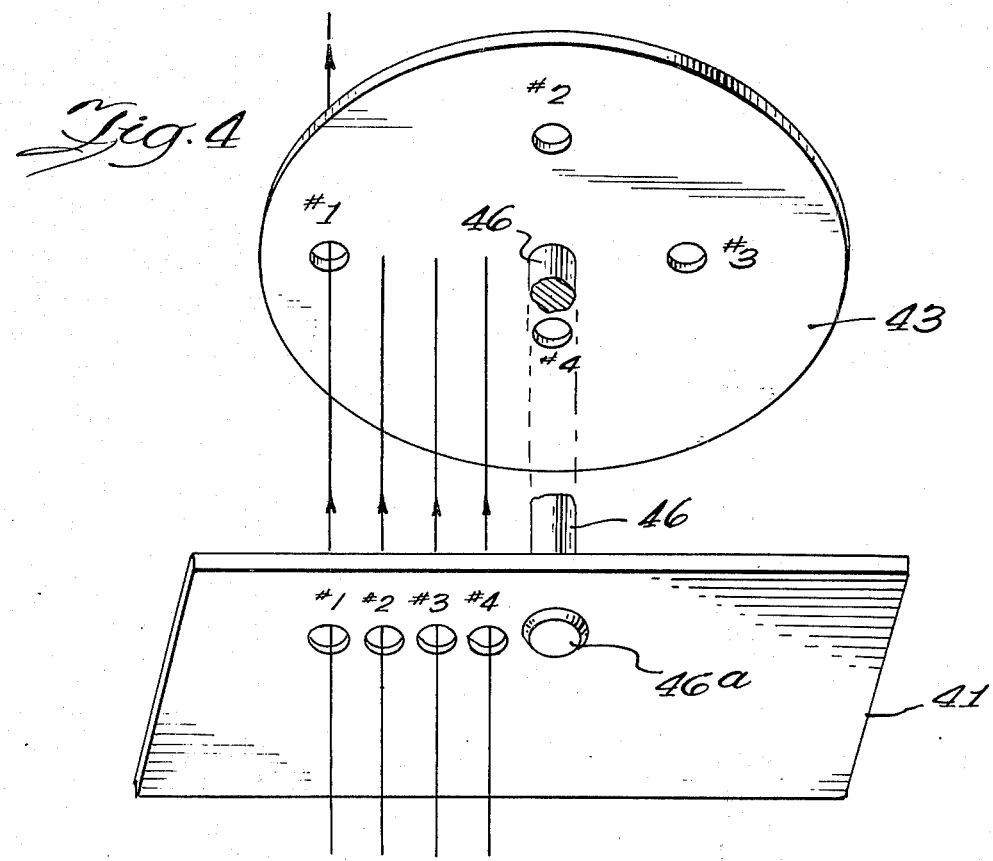
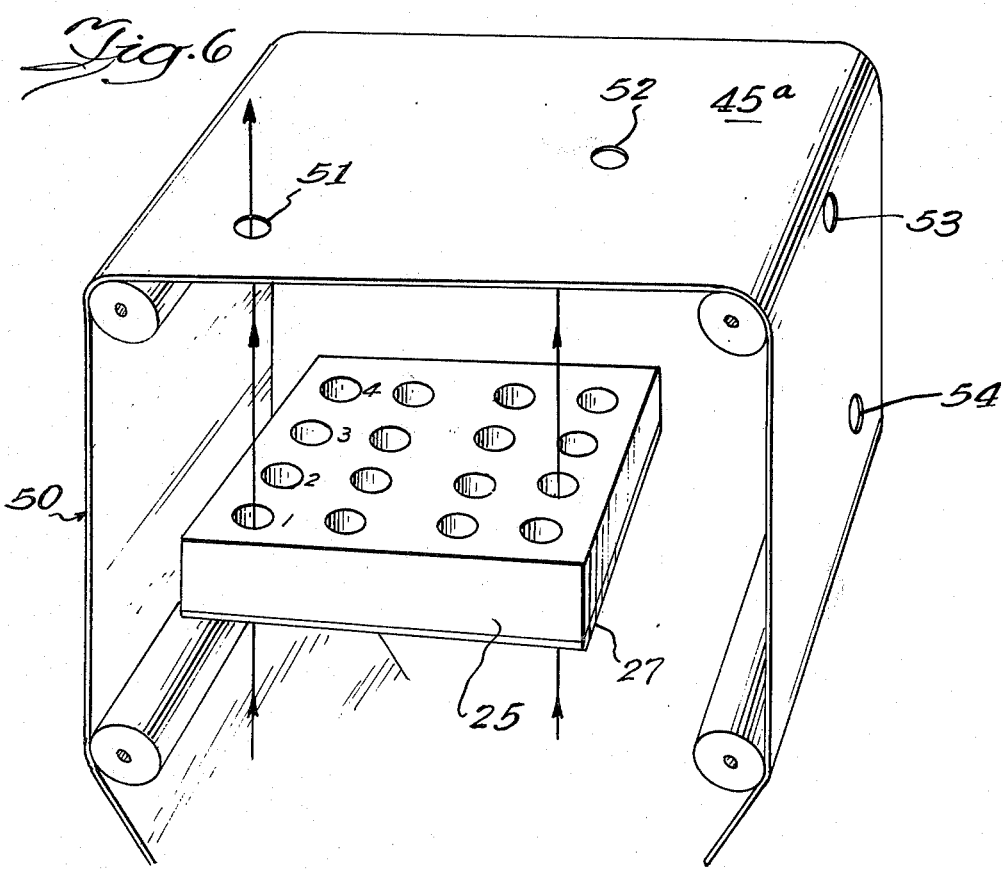

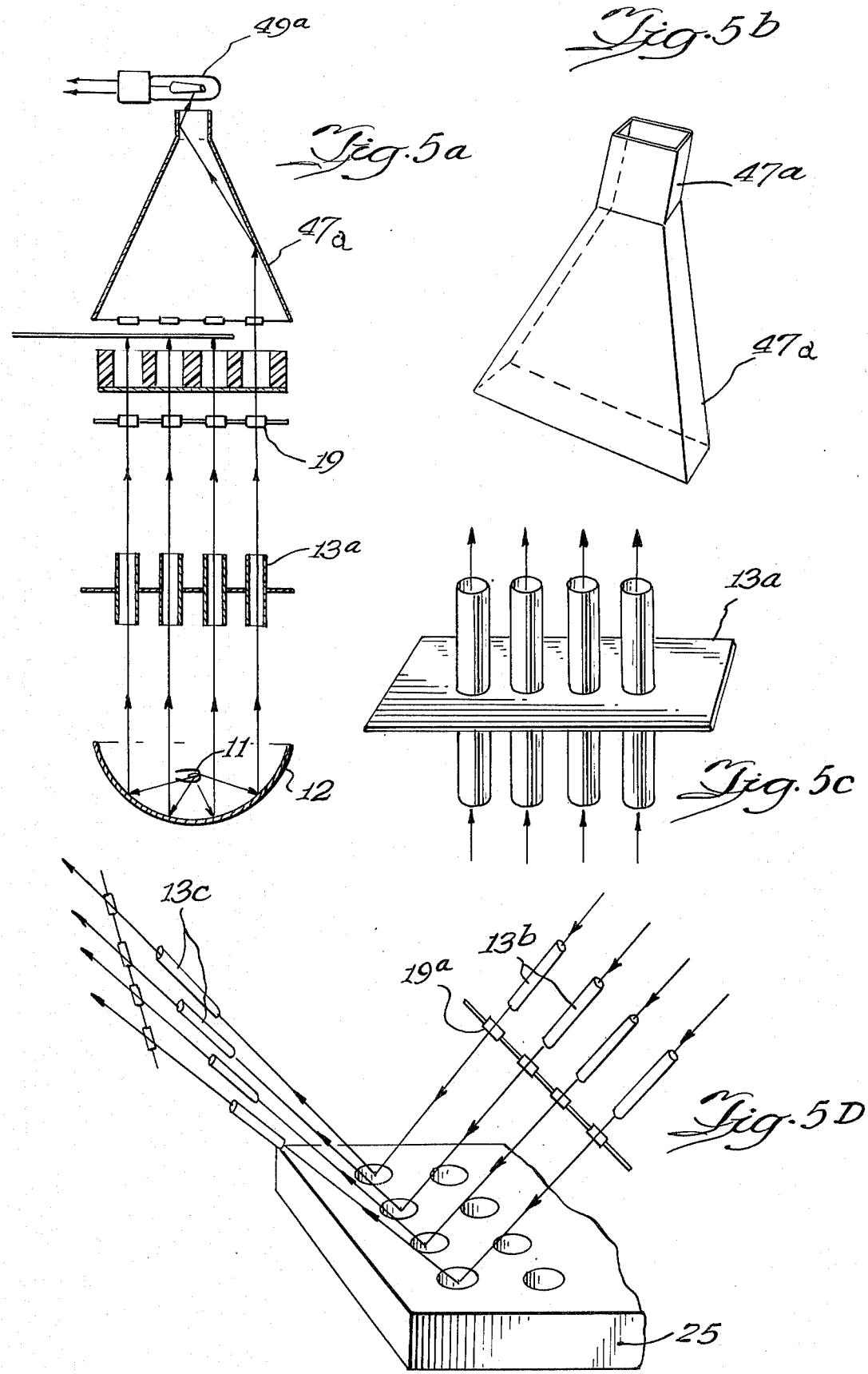

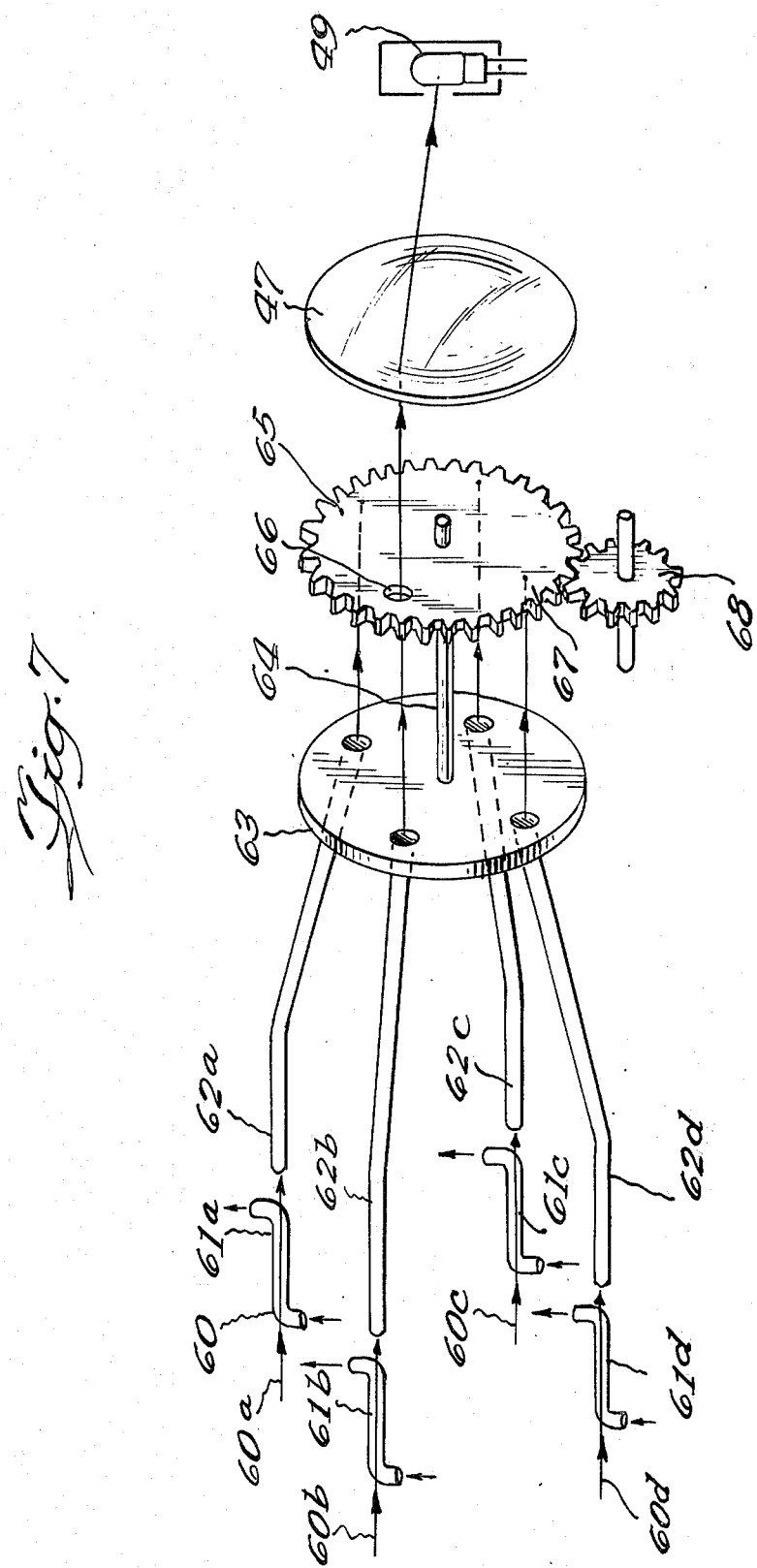

ANALYTICAL MULTIPLE COMPONENT READOUT SYSTEM

BACKGROUND OF THE INVENTION

The present invention relates to chemical analysis and more particularly to the assaying of various components in a solution by evaluating the light intensities arising from a plurality of solutions of the same specimen or sample with different reagents. The invention provides a readout system for measuring changes in light absorbance or fluoroscence of a plurality of solutions for the analysis of their contents.

BRIEF REVIEW OF THE PROBLEM

In analyzing for multiple specimens, there are several procedures being used at present. In one procedure, the samples are disposed around a carousel, and the carousel is rotated on its axis, so that the specimens pass a light source in sequence and intercept a combination of light source and detector both of which are stationary. The light from te cuvettes are then monitored and the results evaluated. This is the principle of U.S. Pat. Nos. 3,489,525, 3,216,804, 3,219,416 and others such as the centrifugal analyzers and also and analyzer called the ABA-analyzer.

Others move either test tubes or cuvettes across a combination of a light source and detector in a linear mode. The test tubes, being transparent, permit the light to pass through. In this way, multiple samples are detected and analyzed. These systems present difficulties when more than one cuvette is in the field at any one time. For example, in multiple analyzers, if there are four cuvettes carrying four different specimens, then one needs four different light sources and four different detectors if they are to be read at the same time. Examples of this are the multiple channel, continuous flow systems of analysis where each stream passes through a flow-through cuvette, similar to that seen in FIG. 11 of U.S. Pat. No. 3,802,782, which then permits the light to go through to a detector. One then has as many detectors as one has flow-through cuvettes.

Another variant is to aspirate the solution into a cuvette. After readout the solution is ejected and the next solution is aspirated. An example of this is U.S. Pat. No. 3,802,782.

In summary, in the past, the cuvettes or the light source or the detector or the solutions have been moved in order to observe specimens in different cuvettes.

SUMMARY OF THE INVENTION

In the present invention, the cuvettes or containers holding the solutions, and the solutions, remain stationary. The light source and the detector also remain stationary, and with a single detector, the multiple samples are read out and the information given to a computer which then analyzes the data in order to print out the computation of the sample. The essence of the invention is the means for the detector looking at the light from each cuvette sequentially. This is done by a disc or belt which moves and uncovers the beam from the various cuvettes sequentially, and then means for directing each beam to the single detector.

The advantage of this system is apparent when one considers that in some multiple channel analyzers, one is dealing with as many as 20 different analyses simultaneously. The present invention has very little limitation on the number of analyses which can be done simultaneously, as will be seen from the specifications below. Large numbers can be read out simultaneously with the scanning devices shown herein.

Generally speaking, the present invention contemplates an arrangement for analyzing a plurality of components in a single specimen which comprises placing a diluted specimen into a storage cup which is part of a sample carrier system, containing a storage cup and reaction cups, transferring aliquots from the storage cup to reaction cups held in rows in a sample carrier. The rows of the sample carrier are then presented to a work station, sequentially adding a reagent to each of the reaction cups and moving the reaction cup into a work field where beams of light passing through the various reaction cups can be scanned and the components contained in the reaction cups can be assayed by means of a single detector attached to a computer and printout system.

The invention, as well as other objects and advantages thereof, will be more apparent from the following detailed description and the accompanying drawings, in which:

BRIEF DESCRIPTION OF THE DRAWINGS

FIG. 3b is a cross sectional view of the type of sample carrier shown in FIG. 3a;

FIG. 4 presents a bottom view of a portion of the inventive concept;

FIG. 5a shows a cross-sectional view of a portion of the inventive concept;

FIG. 5b shows a perspective view of the reflecting chimney of the arrangement of FIG. 5a;

FIG. 5c again illustrates an arrangement in perspective view of collimating tubes for collecting light rays which is useful with the present inventive concept;

FIG. 5d illustrates an arrangement in perspective view of a fluorescence system in the present inventive concept;

FIG. 6 depicts a perspective view of an aspect of the inventive concept;

FIG. 7 shows an additional perspective view to illustrate the principle of the invention; and, FIG. 8 shows a circuit diagram useful with the present invention.

DETAILED DESCRIPTION

Figure 1:
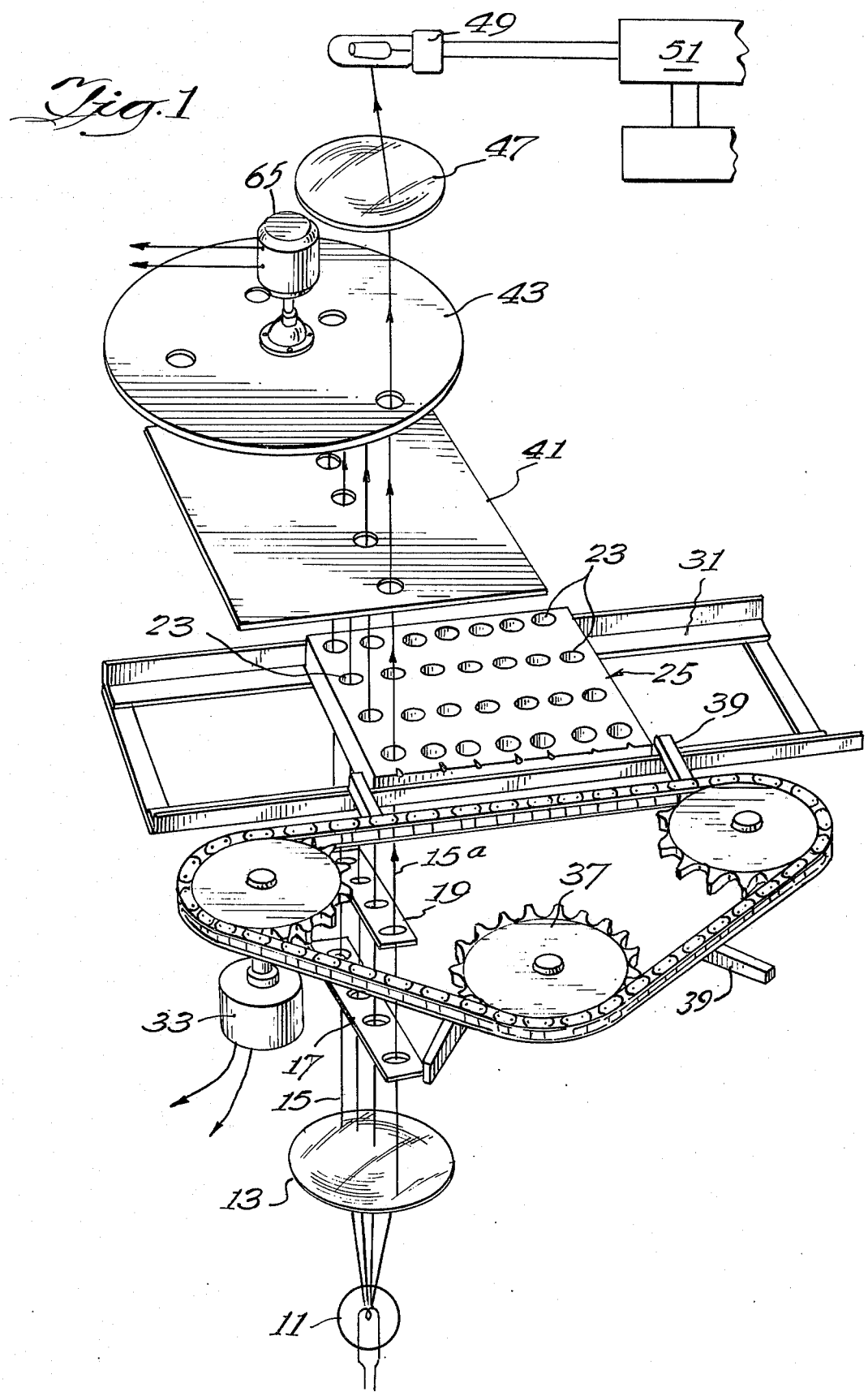
FIG. 1 shows a perspective top view of the arrangement contemplated herein.

The instrument herein contemplated comprises a light source 11 (see FIG. 1), a collimating lens 13 for generating parallel beams of light 15 from the light source.

The parallel beams of light 15 traverse a diaphragm or lower plate with holes 17. This corresponds to the collimating tubes 13a of FIG. 5c resulting in the production of isolated beams of parallel light 15.

The isolated beams of parallel light now traverse light filters 19 to generate parallel beams 15a of monochromatic light radiation.

The object of creating isolated narrow beams 15a of monochromatic light radiation is to have them traverse solutions 21 held in cups 23. These cups are disposed in a sample carrier 25 shown in FIGS. 1, 2.

Figure 2:
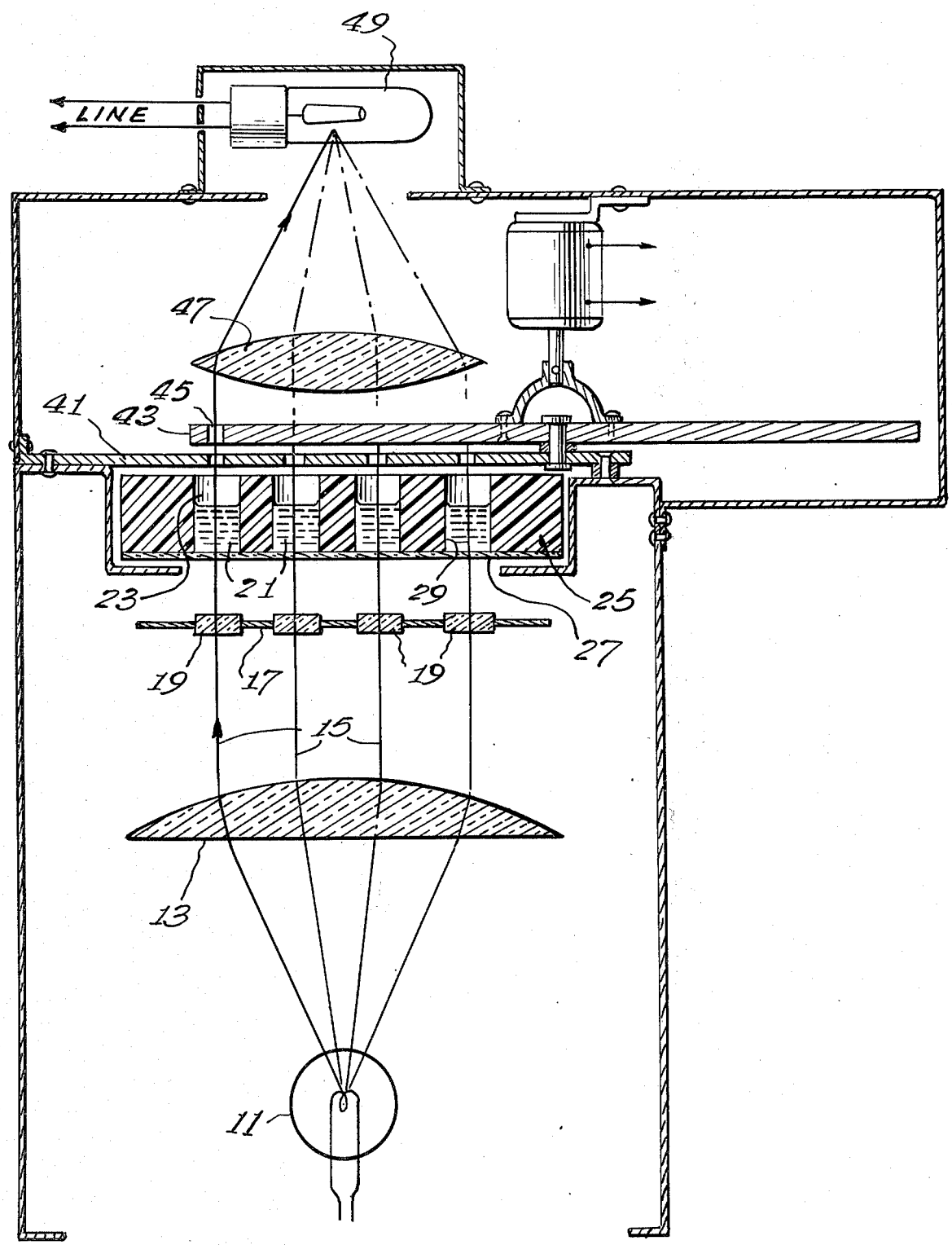
FIG. 2 shows a cross sectional longitudinal side view of the inventive concept.

Referring to FIGS. 1 and 2, a sample carrier is shown made of plastic with a transparent base 27 such as Lucite, poly-styrene or urea formaldehyde resin or glass. The plastic is drilled through to create a plurality of holes arranged in rows. The thin sheet of plastic or glass is then glued to the base to make a plurality of containers. In FIG. 2 a cross-section is shown of the type of sample carrier shown in FIG. 1. In this case, only four chambers are shown each carrying the same sample dissolved with different reagents in order to measure a different component. This corresponds to test tubes held in rows for analysis as have been described in earlier U.S. Pat. Nos. 3,802,782, 3,687,632, and 3,489,525. In FIG. 2, a different type of sample carrier 25a is shown with four reaction cups 29a and a diluting sample cup 29b and a waste cup 29c. The use of this sample carrier will be explained hereinafter.

The sample carrier 25 rests on a sample carrier track 31 and is pushed forward or backward by the action of a drive motor 33 which activates a sprocket and chain assembly, fitted with two idling sprockets 37 and projections from the chain called pushers 39 which can push the sample carrier forward or move it back.

The aforesaid narrow parallel beams of light pass through the solutions contained in the cups containing the solution as in FIG. 2 of U.S. Pat. No. 3,219,416, and then pass through holes in a fixed upper plate 41 on which the scanning disc is mounted. This is detailed in FIG. 4. The scanning disc 43 contains holes 45 corresponding to those in the fixed upper plate 41 but spaced apart so that only one hole 45 of the scanning disc 43 will align with one hole of the fixed upper plate 41 at any time. The fixed upper plate is attached to the scanning disc 43 by a pin or pivot 46 around which the disc 43 can rotate. This is rotated by a timing motor 45. In this way, each of the holes of the fixed upper plate are opened sequentially permitting the light to pass. This can be seen in FIGS. 1, 2 and 4. The pivot 46 is riveted to the fixed plate 46a so that it does not rotate.

In place of the holes, slits, in the form of arcs of approximately 20° may be used. These slits are then not of equal length, the outer slits being larger. This insures that each hole of the fixed upper plate will be open for the same amount of time. If the scanning disc is rotating at 12 r.p.m., this means that light will traverse the cuvette for approximately ¼ of a second.

The light which now emerges from the holes of the fixed upper plate 41 sequentially is focussed by means of a focussing lens 47 on a suitable detector 49 such as a phototube or photomultiplier tube.

The signals from the detector 49 are recorded by a recorder or a computer 51. If a recorder is used, one sees a series of peaks as the opening of the scanning discs passes the opening of the fixed plate 41 and then returns to baseline as the light is cut off. In the case of the computer 51, the peak intensity of the light is recorded for each of the cups in the row. This reading is taken repeatedly for each cup as the scanning disc 43 rotates. Changes in intensity in each cup are noted with time and the reaction is thus monitored separately for each cup. At the end of a chosen number of cycles, the data is analyzed by the computer and printed out as a result in chosen units. A separate result is printed for each cup.

In place of the focussing lens a reflecting chimney 47a may be substituted. This is shown in FIG. 5a in cross section and FIG. 5b is perspective. Each ray of light will be reflected until it reaches the detector 49a. Thus, where ultraviolet or infrared light is used, a lens may be avoided for greater sensitivity. As an alternative to the light chimney or lens, a curved mirror may be placed at an angle to the cups. Light from the cups will then be reflected to a point at which the detector is placed.

Figure 3A:
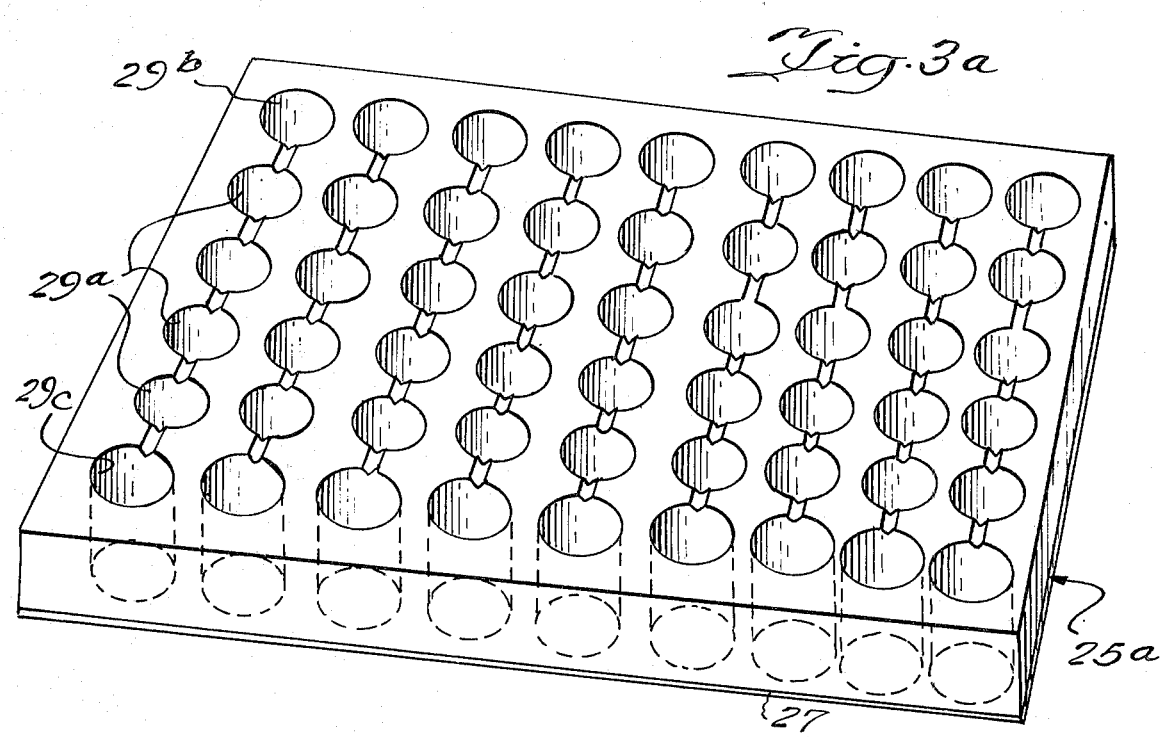
FIG. 3a is a perspective view of a sample carrier useful herein.
Figure 3B:
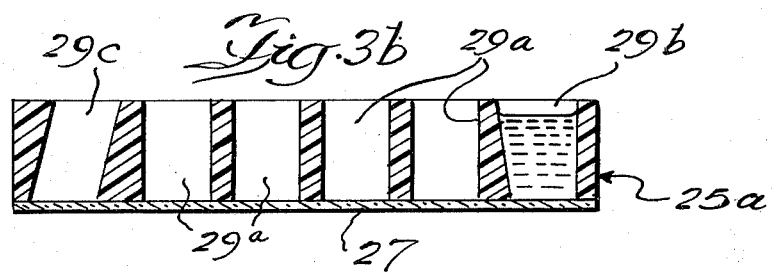
Figure 3C:
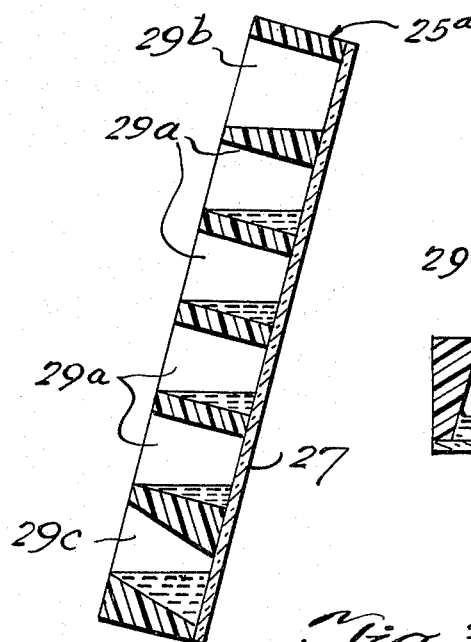
FIG. 3c shows the carrier of FIG. 3b at another instant in time.
Figure 3D:
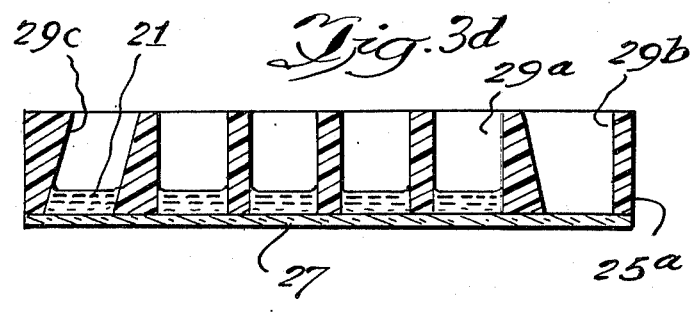
FIG. 3d shows the carrier of FIG. 3b at still another time period.

The operation of the instrument may be described with an example. The rack 25 in FIG. 3a loaded either from a sample diluter as described in U.S. Pat. No. 3,687,632 or from a capillary as described in U.S. Pat. No. 3,859,051 and application Ser. No. 532,947. In either case, the sample carrier is placed in a track. As it advances row by row, a sample or serum to be analyzed plus a diluting fluid is placed in the diluted sample cups of FIG. 3a. Each row now looks like FIG. 3b with the diluted sample in the diluted sample cups. When all of the diluted sample cups are loaded aliquots are taken from the diluted sample cups and distributed to the reaction cups. This may take the form of a dispenser which aspirates the diluted specimen and ejects aliquots into the various reaction cups in the particular row. Another practical procedure is for the operator to tilt the sample carrier as shown in FIG. 3c. This is done automatically by moving the sample carrier along a track which gradually tilts to a position approximately 75° from the horizontal, or the operator slides the rack onto a flat surface tilted at the desired angle. The diluted sample empties from the diluted sample cup 29b which is bucket shaped for this purpose. The diluted sample then runs down a series of tracks to the reaction cups 29a in the same row filling each with a measured amount. The excess runs into the waste cup 29c, drilled at an angle so as to hold the excess more efficiently. On returning to a horizontal position, the sample carrier is shown as in FIG. 3d. The measured samples are in the reaction cups 29a and the excess waste in the waste cup 29c. In this manner, the samples are split into equal parts. The sample in the waste cup is not used further. As an alternative, the cups in a single row may communicate with each other through a small groove at a movable bottom plate. The rack is then held in a horizontal position, aliquots flowing into the various cups in fixed amounts. When the bottom plate is slid over, the grooves are sealed and the aliquots are then isolated.

More conventional means may also be used for dividing the diluted specimen into aliquots. This may take the form as described in U.S. Pat. No. 3,489,525 where a peristaltic pump, with a plurality of tubes, communicates with the diluted specimen, the other end of the tubes being disposed over the reaction cups. When the peristaltic pump is activated, portions of the diluted specimens are distributed to the various cups.

The rack is now placed in the instrument of FIG. 1. Using a multiple dispenser (U.S. Pat. No. 3,837,534) a different reagent is added to each of the four reaction cups 29a. For example, reagent for the assay of four different enzymes in serum is added to each cup in a simple row. These reagents contain NADH (Nicotinamideadenine dinucleotide hydrate). The row is advanced to the readout position and the reaction rate is measured in each cup. In this case a wavelength of 340 nm is used in each case to measure the destruction of the NADH. The drop in absorbance or fluorescence in each cup is measured repetitively. The computer then calculates the slope of the line of the best fit, compares it to a standard curve and prints out a value for each of the enzymes in the same serum.

The same reagents are now added to the second row and the second row moves into readout position. This is repeated until all the rows have been read.

Figure 8:
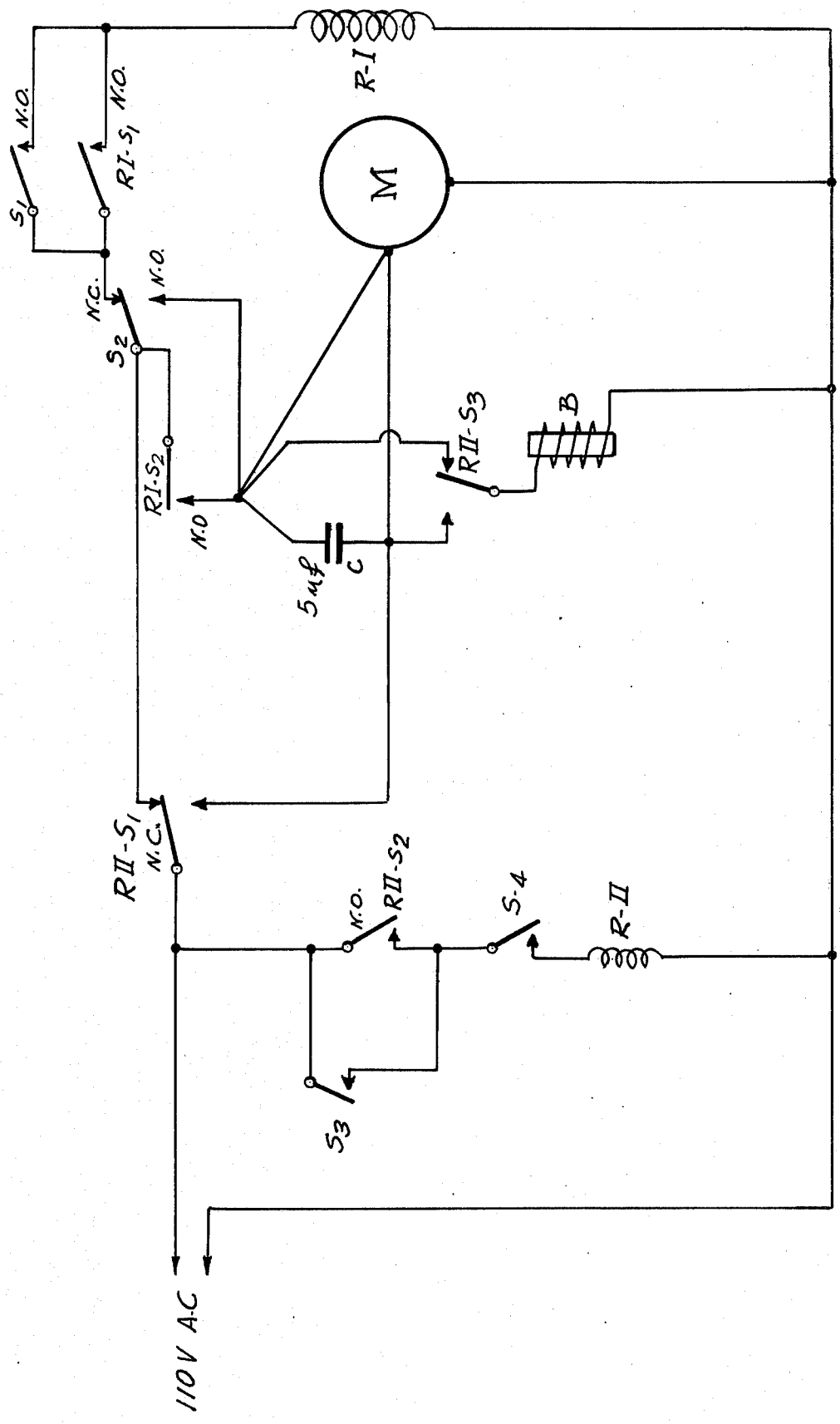

A circuit for movement of the track forward and backward is shown in FIG. 8.

A cam which rotates by means of a timing motor (not shown) closes switch $S_1$ at regular intervals to initiate the cycle. $S_1$ supplies a momentary bypass to RI-$S_1$ locking switch which is in series with the electromagnet R-I. Activation of R-I causes relay locking switch RI-$S_1$ to close and stay closed. This closes relay switch RI-$S_2$ and supplies a bypass so motor M drives the rack forward.

Switch $S_2$ (normally closed) is a switch which slides across the side of the rack. There are depressions alongside the rack so that $S_2$ is alternatively closed or open as it slides across the side of the rack. When the rack is moved to press this switch, the switch is disconnected and moves to the normally open position supplying a bypass to the motor and inactivating relay magnet R-I so that RI-$S_1$ and RI-$S_2$ now return to their original position. The motor M continues to run until switch $S_2$ falls into a depression aligned with the cups in the rack thus returning to its original position. The rack remains in this position until the cam closing switch 51 is activated again and the cycle is repeated.

When the last row of the rack has passed the readout zone, the front of the rack closes reversing switch $S_3$. This activates the second relay RII and moves second relay switches RII-$S_1$, RII-$S_2$ and RII-$S_3$ to their alternate positions. The motor now receives the current from RII-$S_1$ to the opposite side of condenser C, reversing the motor. The rack now moves backward until the rack reaches and opens $S_4$ (normally closed) opens and opens the R-II circuit. This is so because RII-$S_2$ is held down as long as R-II receives power. This returns RII-$S_1$, RII-$S_2$ and RII-$S_3$ to their original positions and the rack can now move forward when $S_1$ is pressed. RII-$S_3$ is the reversing brake switch which permits the current to flow to brake magnet B which stops motor M and prevents coasting, when moving forward or backward.

As an alternative, a turntable with rows of containers with flat bottoms similar to that shown for test tubes in U.S. Pat. No. 3,489,525 may be substituted for the rack. Each row is read as described shifting to the next row for the next specimen. Continuing the circuit a second time will permit the operation as in the foregoing paragraph.

As an alternative, each row is read only once before moving to the next row. After all the rows have been read, the motor is reversed, returning the rack to its original position and the readings are repeated. This can be done repeatedly. After a suitable time, the computer directs the printout to print out the values for all of the specimens at one time. A new sample carrier may then be placed in the machine for readout.

In practice, a speed of 12 rpm is convenient for the scanning disc. Thus, each rotation is 5 seconds. Four readings are taken for each row or one obtains the results at the end of 20 seconds per row. A shift to the next row takes one second. For 16 rows, the elapsed time is then 5⅓ minutes for reading and approximately 16 seconds for shifting from row to row, for a total of less than 6 minutes.

In the alternative mode, each row is read once and then read a second time. The reason that only two readings are needed in the second mode is the fact that sufficient time has elapsed between readings of the same specimens to produce a large change. For 16 rows, the scanning of the sampler carrier takes $16 \times 5 = 80$ seconds. Total elapsed time is 160 seconds for reading and 32 seconds for shifting from row to row, for a total of 192 seconds or approximately 3 1/5 minutes. Thus, this second mode is more rapid.

The most rapid method is to use a larger collimating lens and a large plate with holes containing $16 \times 4 = 64$ holes. The light then passes through all of the samples in the carrier simultaneously. Reagent is added to all cups simultaneously. The rotating discs then contain a spiral of 64 holes resembling the scanning disc in early television models. The entire plate is then scanned simultaneously. At the end of 30 seconds, all of the results are obtained and printed out by the computer. In this case, the sample carrier is merely placed in the field and the instrument reads out all of the specimens without moving the sample carrier. As an alternative, a moving belt No. 50 (FIG. 6) moves in a continuous fashion. Four openings 51, 52, 53 and 54 pass across the rows of the rack exposing the cups in sequence first from the first, then the second, then the third and finally the fourth row. In this way the light ray emerging from each cup is permitted to reach the collimating lens and then the detector. As the belt rotates, each cup is scanned repetitively, so that at the end of 20 seconds each cup has been scanned four times. At higher speeds this can be accomplished in less time. Thus all of the cups may be scanned in 20 seconds. The computer then prints out the data.

FIG. 7 shows a variation of the scanning device similar to the belt described. In the scanning devices described up until now, the disc and the belt contain a multiple series of holes. FIG. 7 shows how this scanning can be done with a single hole in the rotating disc. For example, four light beams, 60a, 60b, 60c and 60d passing through four continuous flow through cuvettes 61a, 61b, 61c, 61d are shown. These are collected by means of optical fibers 62a, 62b, 62c, 62d which guide the light down to the end of the fiber. The use of the fibers permits the disposal of the flow-through cuvettes at convenient positions and in no specific order. The fibers end on a rigid opaque metal holder 63, so that if one is looking at the face of this holder, one would see the lights being produced on the ends of the fibers, changing with a changing flow of solution intercepting the light paths going through the flow cuvettes. Attached to the rigid opaque holder is a rigid axle 64 on which is fitted a wheel 65. Said wheel is a scanning wheel, with a single holes 66. The ends of the optical fibers are arranged at the periphery of a perfect circle, so that this hole will traverse the ends of the optic fibers in sequence. The rotating wheel is edged with gear teeth 67 so that a small gear 68 can engage it and by rotation cause this wheel to rotate on the axle, which is held rigidly by the rigid opaque metal holder. As the wheel rotates, beams of light from the various optic fibers are allowed to pass through this hole in sequence. A focusing lens in back of the rotating wheel permits the focusing of each beam in sequence on the detector. The detector in turn, is attached to the computer and printout, so that the information it obtains can be analyzed in terms of a result for a particular analysis for each of the various flow-through cuvettes.

It will be noted that a reflecting funnel could be substituted for the focussing lens, as shown before. It will also be noted that the optic fibers permit the collection of the information to a small circle so that the scanning wheel, in this particular case, can be small, of the order of one inch, since each of the optic fibers is a few millimeters in diameter, and a substantial number can be disposed around the periphery of a circumference which would be three inches in the case of a one inch diameter circle.

The cups may be scanned electronically, using an arrangement similar to a video camera in place of the scaning disk. In this case, a lens focuses the image of the cups on a light sensitive material containing as many photosensitive cells as there are reaction cups. The cups are illuminated simultaneously from a collimated light source. The photosensitive cells detect the emission from each reaction cup simultaneously, but the computer monitors their output sequentially similar to sending a television signal through space.

It is to be observed therefore, that according to the present inventive concept, the following matters are taken into consideration.

1. The specimens, in their containers, are transmitting or emitting light. In the case of light which has been passed through them, they absorb some of the light. In the case of fluorescence, they are irradiated with one wave length, such as ultraviolet, and give off visible light. Therefore, each of the cuvettes can be considered as a source of light.

2. The beams of light coming from the cuvettes are collimated.

3. They are made to go through an opening which changes its position sequentially so that it goes from curvette to cuvette allowing a beam of light to go through to a detector. In short, the light coming from the various cuvettes are being scanned in the same way as one scans a picture for the purposes of broadcasting television.

4. Once these beams of light pass the opening sequentially, they are then directed to a single detector, which does not move, and then read out by a computer taking the data and printing it in terms of concentration.

In the prior art, the cuvettes moved past a light source with a detector on the other side, so that the light source and the detectors are stationary, but the cuvettes are moving. Also, some aspirate a solution sequentially into a cuvette. Generally speaking, these are the most common systems used. The alternative is to use as may light sources and as many detectors as there ae cuvettes. According to the present invention, the cuvettes do not move, the solutions do not move and the light source does not move and the detector does not move.

In the present invention, there are several types of scanning means; which are essentially equivalent, for example.

1. The belt with as many holes as rows
2. the disc with as many holes as samples in each row
3. A disc and light fiber assembly where the rotating disc has only one hole.

I claim:

1. In an analytical chemical system, an instrument for rapidly analyzing a plurality of components in a single specimen by the measurement of the light intensity emitted from a plurality of solutions using a single detector and light source, so as to translate these light intensities in terms of concentration of chemical components in these solutions, comprising
    a. a carrier and travel means, said carrier having a plurality of sample containers in rows thereon disposed to carry said containers which are to hold a specimen along a travel path by said travel means;
    b. a work station along said travel path having a light source thereat;
    c. light collimating means at said work station for collimating the light emitted from said light source to produce a first beam of the same color as said emitted light;
    d. light selection means disposed for receiving said first beam, for selecting a monochromatic beam of light from said collimated light source to produce a second beam;
    e. light isolating means for isolating a plurality of narrow third light beams from said collimated monochromatic second beam so disposed as to pass each of these third light beams in a plane through solutions in said plurality of containers so that part of the light is absorbed by samples therein and part transmitted;
    f. detector means and focusing means for focusing said transmitted third light beams so as to converge said third light beams to said detector means;
    g. interruption scanning means for scanning each of said transmitted third light beams emerging from said solutions sequentially so that said detector means receives said narrow light beams in sequence, said interruption scanning means comprising a disk rotatable about an axis, said disk having a plurality of holes at different radii from the axis of rotation of said disk, each disk positioned to interrupt said transmitted third light beams substantially perpendicular to the plane defined by said transmitted third light beams, wherein said disc sequentially scans a row of sample containers by rotating said disk with respect to said transmitted third light beams; and
    h. light reading means for translating the signals of the detector to a written record.

2. A device as claimed in claim 1 including light measuring means in said detector where light traverses each container and differences in absorbed light are being measured.

3. A device as claimed in claim 1, said light means being ultraviolet light means and the ultraviolet light irridates the solution in the container causing it to fluoresce and emit light.

4. The instrument of claim 1, where the absorbed beam of monochromatic light causes the solution to fluoresce emitting a longer wavelength than that absorbed, said instrument including a secondary set of light filters fitted between said containers and said detector means so as to transmit only the longer wavelength.

5. The instrument of claim 1, wherein said travel means present each row sequentially to said work station, the containers in each row being scanned in sequence thereof so as to present the light emitted from said containers to a single detector.

6. The instrument of claim 1, the means for collimating the beam of light being a lens.

7. The instrument of claim 1, the means for collimating the beam of light being a combination of a reflector and collimating tubes.

8. The instrument of claim 1, said carrier having a transparent base, the samples being disposed in rows in the said carrier.

9. The instrument of claim 1, wherein sad light reading means for producing the written record from the signals of the detector is a recorder.

10. The instrument of claim 1, where the light reading means for producing the written record is a computer with a printout system.

11. A device as claimed in claim 1, wherein said focusing means is a lens.

12. A device as claimed in claim 1, wherein said focusing means is a light chimney.

13. A device as claimed in claim 1, wherein said focusing means comprises light pipes and a lens.

14. A device as claimed in claim 1, wherein said focusing means comprises a fiber optic bundle and a lens.

15. In an analytical chemical system, an instrument for rapidly analyzing a plurality of components in a single specimen by the measurement of the light intensity emitted from a plurality of solutions using a single detector and light source, so as to translate these light intensities in terms of concentration of chemical components in these solutions, comprising a. a carrier and travel means, said carrier having a plurality of sample containers in rows thereon disposed to carry said containers which are to hold a specimen along a travel path by said travel means;

b. a work station along said travel path having a light sorce thereat;

c. light collimating means at said work station for collimating the light emitted from said light source to produce a first beam of the same color as said emitted light;

d. light selection menas disposed for receiving said first beam, for selecting a monochromatic beam of light from said collimated light source to produce a second beam;

e. light isolating means for isolating a plurality of narrow third light beams from said collimated monchromatic second beam so disposed as to pass each of these third light beams through solutions in said plurality of containers so that part of the light is absorbed by samples therein and part transmitted;

f. detector means and focusing means for focusing said transmitted third light beams so as to converge said third light beams to said detector means;

g. interruption scanning means for interrupting the transmitted third light beams including a moving belt with holes, the light being interrupted sequentially by said moving belt with holes so that the rows of sample containers may be read out sequentially; and h. light reading means for translating the signals of the detector to a written record.

* * * * *